(12) United States Patent
Keall et al.

(10) Patent No.: US 7,469,035 B2
(45) Date of Patent: Dec. 23, 2008

(54) METHOD TO TRACK THREE-DIMENSIONAL TARGET MOTION WITH A DYNAMICAL MULTI-LEAF COLLIMATOR

(75) Inventors: Paul J. Keall, Stanford, CA (US); Amit Sawant, Los Altos, CA (US); Yelin Suh, Stanford, CA (US); Sergey Povzner, Burlingame, CA (US); Herbert Cattell, Mountain View, CA (US)

(73) Assignees: The Board of Trustees of the Leland Stanford Junior University, Palo Alto, CA (US); Varian Medical Systems Technologies, Inc., Palo Alto, CA (US)

( * ) Notice: Subject to any disclaimer, the term of this patent is extended or adjusted under 35 U.S.C. 154(b) by 0 days.

(21) Appl. No.: 12/001,762

(22) Filed: Dec. 11, 2007

(65) Prior Publication Data

US 2008/0159478 A1   Jul. 3, 2008

Related U.S. Application Data

(60) Provisional application No. 60/874,314, filed on Dec. 11, 2006.

(51) Int. Cl.
*A61N 5/10* (2006.01)

(52) U.S. Cl. .......................... 378/65; 378/205
(58) Field of Classification Search .................. 378/65, 378/205, 152

See application file for complete search history.

(56) References Cited

U.S. PATENT DOCUMENTS

| | | | |
|---|---|---|---|
| 6,501,981 B1 | 12/2002 | Schweikard et al. | |
| 7,085,348 B2 * | 8/2006 | Kamath et al. | 378/65 |
| 7,221,733 B1 * | 5/2007 | Takai et al. | 378/65 |
| 7,295,649 B2 | 11/2007 | Johnsen | |
| 2005/0123098 A1 * | 6/2005 | Wang et al. | 378/151 |
| 2007/0064871 A1 * | 3/2007 | Earl et al. | 378/65 |

* cited by examiner

*Primary Examiner*—Hoon Song
(74) *Attorney, Agent, or Firm*—Lument Patent Firm (57) ABSTRACT

A method of continuous real-time monitoring and positioning of multi-leaf collimators during on and off radiation exposure conditions of radiation therapy to account for target motion relative to a radiation beam is provided. A prediction algorithm estimates future positions of a target relative to the radiation source. Target geometry and orientation are determined relative to the radiation source. Target, treatment plan, and leaf width data, and temporal interpolations of radiation doses are sent to the controller. Coordinates having an origin at an isocenter of the isocentric plane establish initial aperture end positions of the leaves that is provided to the controller, where motors to position the MLC midpoint aperture ends according to the position and target information. Each aperture end intersects a single point of a convolution of the target and the isocenter of the isocentric plane. Radiation source hold-conditions are provided according to predetermined undesirable operational and/or treatment states.

8 Claims, 11 Drawing Sheets

(a)
FIG. 1

Prior Art

METHOD TO TRACK THREE-DIMENSIONAL TARGET MOTION WITH A DYNAMICAL MULTI-LEAF COLLIMATOR

CROSS-REFERENCE TO RELATED APPLICATIONS

This application is cross-referenced to and claims the benefit from U.S. Provisional Patent Application 60/874,314 filed Dec. 11, 2006, which is hereby incorporated by reference.

FEDERALLY-SPONSORED RESEARCH OR DEVELOPMENT

This invention was made with Government support under contract CA093626 awarded by the National Institutes of Health. The Government has certain rights in this invention.

FIELD OF THE INVENTION

The present invention relates generally to radiation therapy. More particularly, the present invention relates to tracking of three-dimensional (3D) target and normal tissue motion and deformation with a dynamic multi-leaf collimator.

BACKGROUND

When beams of high energy x-rays or electrons are used for radiotherapy, it is important to direct the beams to a tumor within the patient, while restricting the beams from striking healthy tissue outside the tumor region. Tumors commonly have irregular shapes and it is necessary to shape the beam cross-section to the corresponding irregular shape. It is common for a treatment plan to prescribe the beam to be directed at the tumor from a number of different angles, where the beam profile is unique for each corresponding angle.

In an attempt to alleviate the need to fabricate a unique aperture for each exposure, multi-leaf collimators (MLC) have been implemented as a way to shape the radiation beam cross-section for radiotherapy treatments. These devices include a set of flat, thin leaves made from a high-density material, such as tungsten, where each leaf is moved transversely in and out of the radiation field to selectively attenuate portions of the beam to create a unique beam cross-section. The shape of the beam can be altered dynamically during the therapy session using motorized controls connected to each leaf. By dynamically attenuating select portions of the beam, intensity-modulated radiotherapy (IMRT) has been made possible, where by moving the leaves during beam exposure, the beam can be delivered in a manner such that the spatial fluence of the irradiation is not constant over the irradiated area.

IMRT can also be accomplished by making multiple irradiations, each with a different field shape, the sum of which creates a field of non-uniform intensity. The leaves must be thick enough to highly attenuate the beam.

In accordance with some accelerators, the MLC has been used to replace the standard field-shaping jaws of a beam accelerator. The shape of the portion of the leaf that defines the edge of the field is designed for minimum penumbra to create the sharpest edge of the beam as possible between the irradiated and protected areas.

The goal of radiotherapy is to deliver a radiation dose to the tumor while minimizing radiation-induced damage to surrounding normal tissue and organs. Accomplishing these tasks includes providing an imaging scheme to plan the treatment and an imaging scheme to ensure accurate delivery of the planned treatment.

The effectiveness of radiation treatment depends on the accuracy of providing an appropriate radiation dose to the target using geometric and dosimetric configurations, and upon the precision of repeated dose delivery. Radiotherapy is typically performed in multiple sessions spread over a period of several weeks, with each session having multiple dose fractions delivered from different beam angles. In an ideal situation, the patient's internal anatomy as well as their placement with respect to the beam would be constant throughout the course of the treatment and identical to the geometry that was recorded for generating the treatment plan. In practice, significant deviations in patient geometry can occur both between dose fractions (interfraction) and within a single fraction (intrafraction).

Interfraction deviations can cause interfraction errors during the beam delivery in a time span as short as between dose fractions, where the deviations occur from systematic changes in the internal anatomy such as tumor shrinkage and/or tissue shrinkage, or patient-initiated movement to achieve a more comfortable position. Various forms of in-room, 2D imaging (e.g., MV x-ray imaging, orthogonal kV x-ray imaging) and 3D imaging (e.g., cone-beam kV and MV CT, 3D ultrasound, and optical position monitoring) strategies have been employed in order to monitor and minimize such interfraction deviations.

Deviations in intrafraction geometry occur primarily from some form of physiological process such as respiration, cardiac motion, bladder filling, and movement of rectal gas, or by patient-initiated motion during system operation, referred to as "Beam-ON". Such deviations can result in significant changes in the position and the shape the tumor target as well as the surrounding anatomical structures, causing significant geometric and dosimetric uncertainties in both treatment planning and dose delivery. Thus, insufficient dose may be delivered to the tumor target(s) and/or high levels of dose may inadvertently be delivered to healthy tissue and critical organs. While these problems have been long recognized, it is only recently that increasing attention has been directed toward the effective management of intrafraction motion, particularly, in the context of treating thoracic and abdominal tumors.

Currently, the approach used to account for all forms of geometric uncertainty in radiotherapy is to add a margin around the volume to be irradiated, also called the clinical target volume (CTV) to create a larger planning target volume (PTV) that accommodates the geometric uncertainties due to intrafraction and interfraction related deviations. In the case of intrafraction motion, the range of motion can be estimated using fluoroscopy or 4D CT scans in order to determine the required margins so as to maintain the target in the beam trajectory at all times.

While the use of 4D image-guidance in defining the PTV margin is a useful approach, this strategy has two limitations. First, even with image-guidance, a motion inclusive margin results in significant volumes of healthy tissue around the target receive unnecessary radiation. Furthermore, this "no-feedback" strategy incorrectly assumes that motion observed in the 4D planning images is reproducible and correctly reflects motion during dose delivery.

A prominent intrafraction geometric deviation arises from patient respiration when treating thoracic and abdominal tumors. Some intrafraction motion management strategies have been implemented in an attempt to minimize or eliminate these deviations, such as abdominal compression, or instructing the patient to breath-hold during a chosen respiratory phase or to perform shallow breathing. All of these techniques have been reported to reduce target motion and, thereby, yield lower geometric uncertainty in planning and delivery. However, the success of these techniques is heavily predicated on patient compliance with instructions, which may not be possible for lung cancer patients exhibiting compromised lung function or having significant discomfort.

In order to address some of the limitations of the strategies described above, many groups have worked on approaches that are based on allowing intrafraction motion and adapting treatment planning and/or treatment delivery to accommodate the resulting geometric deviations. In these approaches, the problem of motion management involves two independent tasks: real-time estimation of target position and shape and, real-time beam adaptation through reshaping of the treatment beam relative to the estimated target position/shape.

In this discussion, the term real-time is used to denote a time duration that is much less than the time scale of the motion being studied. Additionally, the terms beam adaptation and adaptive radiotherapy are used to indicate a dynamic change in the delivered fluence through modifying the geometric shape of the beam aperture.

Real-time motion monitoring of the tumor target(s) can be performed using external markers, internal markers and/or internal anatomical features. Systems that use external markers are based on infrared LEDs or reflective markers placed on the patient and imaged continuously with a video camera, or by using systems that monitor respiratory motion using spirometry or a wraparound strain gauge. Most of the systems that use internal markers are based on frequent monoscopic or stereoscopic x-ray imaging of radio-opaque markers that are surgically implanted near the tumor target. A system based on electromagnetically-excitable, implanted transponders has been reported for real-time monitoring of prostate motion.

While external markers have been found to be well correlated with internal anatomy within an imaging session, there is no guarantee that these correlations will continue to exist and be constant throughout the course of the therapy. For example, even with precise patient localization, uncertainties in external marker-based monitoring may arise from (a) changes in patient anatomy (e.g., weight loss) and (b) day-to-day variations in marker placement. Further, it is difficult to use external markers to provide information about target deformation, or about dissimilar motion of multiple targets. In general, implanted, radio-opaque seeds have been found to be more reliable than external markers. However, in order to obtain high-quality real-time information about the target from radio-opaque markers, it is necessary to perform fluoroscopic x-ray imaging, resulting in increased patient dose. For this reason "hybrid strategies" that primarily use external surrogates and periodically update the position information using x-ray images of implanted markers are being attempted to overcome these issues. The situation is somewhat better with implanted electromagnetic transponders, which do not involve ionizing radiation. However, implantation of fiducials, whether radio-opaque or electromagnetic, is necessarily invasive and carries with it the risk of associated complications—an issue that becomes especially important for cancer patients with weakened systems.

Techniques attempting to perform beam adaptation are based on beam gating or continuous motion tracking. Gating is almost exclusively employed to account for respiratory motion, which tends to be periodic or quasi-periodic. From the information provided by the position monitoring system, the treatment beam is switched on during a pre-defined gating "window". This temporal window (typically, 30 to 50% of the respiratory cycle) may be based on the time-varying positional changes as recorded by the monitoring system or on the respiratory phase calculated from the position information. Currently, gating, based on continuous position monitoring external, is considered the method of choice for the management of respiratory motion, however dosimetric variations remain as yet an unresolved problem due to variations in the breathing cycle by the patient.

Among the various strategies for beam adaptation, respiratory gating, used in conjunction with respiratory-correlated 4D CT, is arguably the most widely implemented. Despite promising results, there remains a major weakness in that gating assumes that target motion observed in planning images (typically acquired over one to three respiratory cycles) accurately and consistently represents motion over several respiratory cycles during delivery. This assumption need not hold true even within the same treatment session due to changes in patient's breathing pattern. Such changes include increase/decrease in breathing volume, or changes in the displacement and phase relationship between the surrogate and the tumor. Furthermore, the relatively low efficiency of gating (~30 to 50%) when combined with that of IMRT delivery (~20 to 50%) can result in 4 to 15 times increase in delivery time. Consequently, the tumor control efficacy of such prolonged treatments can potentially be compromised due to intrafraction repair of sub-lethally damaged tumor cells.

Tracking, in contrast to gating, uses a radiation beam for irradiating a target through a multiple leaf collimator (MLC), for collimating and adjusting the shape of the radiation beam projected onto the target. An image detector detects the image beam and generates an image signal of the target. The target signal is used to generate a beam adjustment signal for controlling the beam adjuster, thereby enabling the radiation beam generated by the radiation source to track the target. Other employed (x-ray) beam tracking strategies are based on a combination of a movable remote-controlled patient couch, a light-weight linear accelerator mounted on a robotic arm, and moving aperture(s) created by adjusting the MLC. However real-time tracking during treatment remains a real problem due to an inherent latency of the combined systems.

Limitations in the utility of current motion monitoring techniques include reliance on surrogates, assuming that these accurately represent internal target motion, monitoring only the target centroid for a single target and, in imposed "cost" upon the patient due to increased imaging dose and/or interventional complications.

Tumor tracking using a MLC is of much interest for intrafraction motion management in thoracic and abdominal cancer radiotherapy to overcome the significant geometric and dosimetric uncertainties in radiation treatment planning and dose delivery. Thus the need for achieving greater geometric precision in treatment planning and delivery is well recognized. It is highly desirable to routinely achieving sub-millimeter targeting accuracy during dose delivery.

Accordingly, there is a need to develop a robust, dynamic multi-leaf collimator (DMLC) tracking algorithm that obtains real-time information of the location shape, size and orientation of the target and surrounding anatomy from one or more independent position monitoring systems, and dynamically repositions the beam to account for real-time 3D motion and deformation of one or more targets and the surrounding anatomy including one or more critical organs, for the purpose of conformal intensity modulated radiotherapy (IMRT) and/or dynamic volumetric arc-based radiation delivery using x-ray or particle beams to account for the above-mentioned motion and deformation of the targets and the surrounding anatomy.

SUMMARY OF THE INVENTION

The current invention provides a method of continuous real-time monitoring and positioning of multi-leaf collimators during on and off radiation exposure conditions of radiation therapy treatment in order to account real-time changes in the shape and position of the tumor target and anatomical surrounding anatomical structures relative to a radiation beam. The method includes using a prediction algorithm with a controller to estimate a future position of the target in relation to the radiation source reference frame. The method also includes the steps of determining the position, size, shape and orientation of the target according to the frame of reference of the radiation source, by dynamically accounting for the instantaneous angular orientation of the LINAC gantry as well as that of the MLC. Further, the method provides the determined target information to the controller, and determines the initial position of each leaf of the MLC. The method further provides a treatment plan to the controller from a treatment plan data file. Temporal interpolations of radiation doses are provided according to the treatment plan, where predetermined positions of the leaves are provided that correlate to radiation dose segments along a total duration of a total irradiation of the target. Cartesian coordinates having an origin at an isocenter of the isocentric plane are used to establish an initial position of the aperture ends of the leaves.

The isocentric plane is defined as the plane perpendicular to the principal axis of the radiation source. The initial position information of the aperture ends is provided to the controller. The aperture end width and aperture end midpoint for each the leaf are determined. The width and midpoint information is provided to the controller, where the controller directs motors to position the MLC midpoint aperture ends according to the initial leaf position information derived from the treatment plan and the real-time target (and surrounding anatomical) position information provided by one or more position monitoring systems. Each aperture end midpoint is positioned in order to modify the radiation aperture so as to optimally deliver the intended radiation dose to the target while avoiding dose to surrounding anatomical structures, where the aperture end midpoint is positioned to intersect a single point of a convolution of the target and the isocenter of the isocentric plane. Further, radiation beam hold-conditions are provided, where the hold-condition is according to predetermined undesirable operational and/or treatment states.

In another embodiment of the invention, the method includes dynamically moving the MLC carriages (which hold each leaf bank) in the direction perpendicular to leaf motion in order to track the principal component of motion along the direction perpendicular to MLC leaf motion and moving a plurality of MLC leaves in the manner described above in order to account for components of target and anatomical motion along the direction of leaf travel.

In one embodiment of the invention, the method further includes calculating the optimal position of radiation source jaws, where the jaw position optimization includes using Cartesian coordinates in a plane that is transverse to the radiation source having an origin concentric to the source to determine initial positions of the jaw, providing the jaw positions to the controller, dynamically positioning the exposure ends of the jaws, where the jaw ends are positioned proximal to the aperture ends of the MLC. In one aspect of the current embodiment, the proximal position can be from 0 to 20 leaf widths along a first axis of the jaw coordinate system and from 0 to a maximum travel range of the leaf along a second axis of the jaw coordinate system.

In one aspect of the current invention, the prediction algorithm may include neural networks, autoregressive moving average models, modified linear adaptive filter, adaptive or Kalman filters.

In another aspect of the invention, the target position, size and shape determination includes determining an initial position of the target by monitoring at least one external target marker and at least one internal marker, using a position prediction algorithm to estimate a future position of the target, using a rotation matrix to calculate rotational changes in the position of the target relative to the radiation source, using Cartesian coordinates along an MLC plane to calculate an X-offset and a Y-offset of the target, where the offsets result from movement of the target along a path of the radiation source, and using Cartesian coordinates along an isocentric plane of the target to calculate an X-translation and a Y-translation of the target.

In another aspect of the invention, a predetermined undesirable operational and/or treatment state may include when the target moves below one or more the jaws, when the leaf aperture end intersects more than a single point of the convolution of the target and the isocenter of the isocentric plane, when no the apertures exist in the MLC plane, when any the leaves in a leaf pair overlap, or when said leaves are separated more that a maximum allowable distance.

In a further embodiment, the radiation beam is a particle beam, where the continuous real-time beam positioning is performed using a particle actuator that shapes the particle beam according to the convolution of the target and the isocenter of the isocentric plane.

BRIEF DESCRIPTION OF THE FIGURES

The objectives and advantages of the present invention will be understood by reading the following detailed description in conjunction with the drawing, in which.

DETAILED DESCRIPTION OF THE INVENTION

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

The current invention advances the ultimate objective of image guidance in radiotherapy by accurately hitting the tumor without imposing any extra "cost" (such as surgical implantation of markers and/or x-ray imaging) upon the patient, where radiotherapy is defined as the use of some form of ionizing radiation including but not limited to photons, electrons, protons and ions. The current invention provides continuous, high-quality position monitoring combined with real-time beam adaptation.

The present invention provides a new method for controlling, in real-time, an aperture profile of a dynamic multi-leaf collimator (DMLC) based on 3-D tracking of a treatment target. The invention is especially useful for the treatment of tumors, which move due to respiratory, cardiac, skeletal or gastrointestinal-induced motion during cancer radiotherapy.

The invention obtains real-time information of target location, size, shape and orientation from an independent position monitoring system and dynamically calculates MLC leaf positions to account for target dynamics. The current invention provides DMLC tracking with sub-millimeter geometric accuracy in all three dimensions. Significant dosimetric improvements are attained in conformal and IMRT deliveries to moving targets are provided by the aspects of the current invention.

According to the current invention the continuous target tracking has several distinct advantages over other techniques. First, unlike gating, the tracking approach aims to use 100% of the position information obtained from the real-time monitoring system, resulting in less residual motion and less time for tumor cell repair from sub-lethal damage. Second, the property of a tracking system to keep the target in the beam's view at all times can be exploited to great advantage during 4D treatment planning as well as delivery for periodic or quasi-periodic motion. For example, in each respiratory phase, the dose to the target can be escalated or reduced depending on the absence or presence of critical structures in the beam's line-of-sight.

The key advantage of the MLC-based approach of the current invention is that each leaf is controlled independently and can be considered as a degree of freedom for repositioning and, potentially, reoptimization. Therefore, unlike techniques which track the centroid of a single target using a robotic LINAC or dynamic couch repositioning (which can also cause patient discomfort), DMLC tracking can be used to account for translation, rotation and deformation of one or multiple targets as well as surrounding anatomical structures. This allows for fully exploiting the volumetric information obtained from fast cine MR images.

Figure 1:
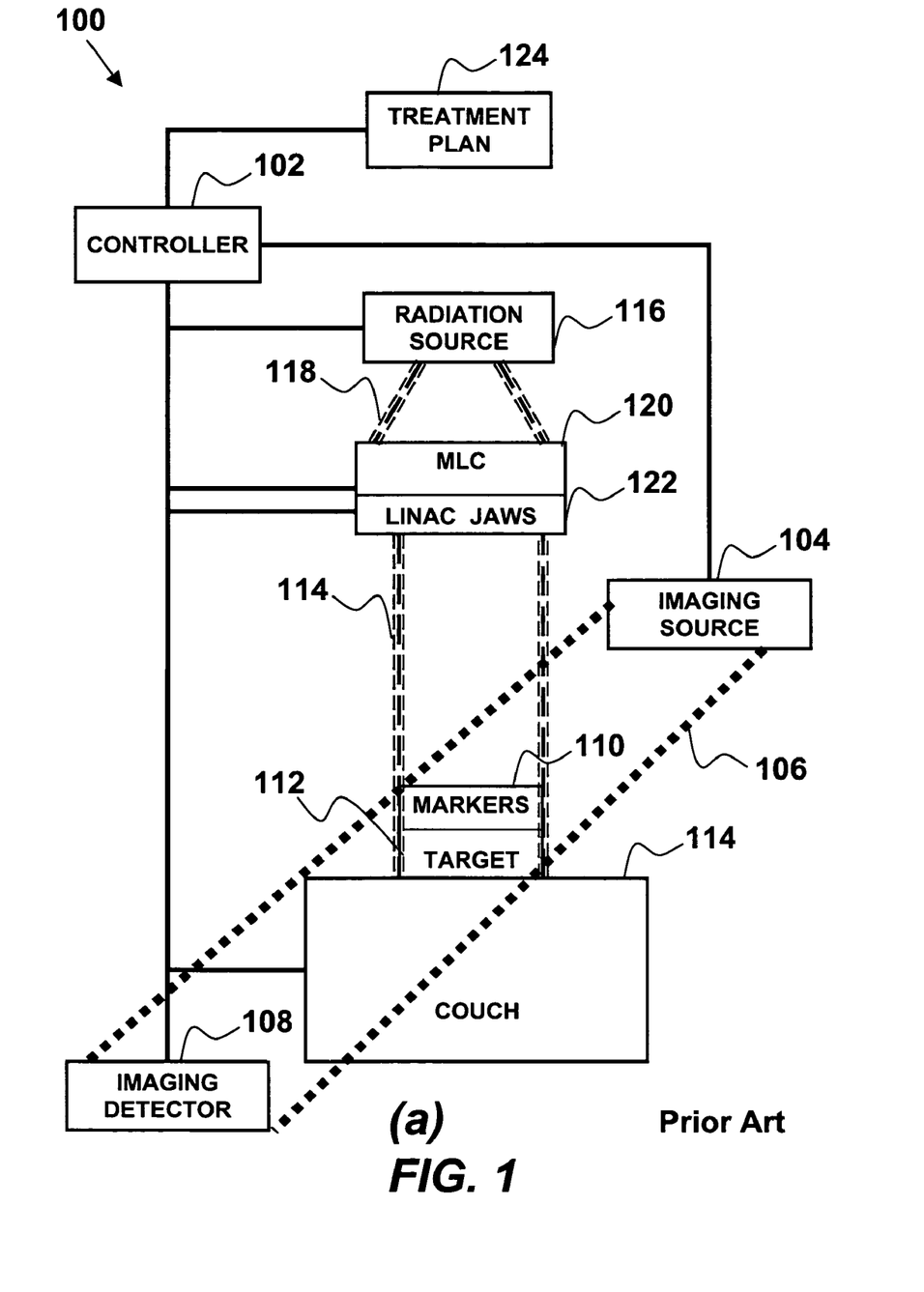
FIG. 1(a) shows a schematic diagram of a typical radiation therapy treatment system.
FIG. 1(b) shows a typical MLC having an aperture surrounding a target.

Referring now to the figures, FIG. 1(a) shows a schematic diagram of a prior art radiation therapy treatment system 100, where shown is controller 102 for managing the system operation. The controller 102 provides signaling information to an imaging source 104 that casts an imaging signal 106 to an imaging detector 108. Disposed along the path of the imaging signal 106 is at least one marker 110 that is proximal to at least one target 112, where the markers 110 and targets 112 are stationed on a couch 114. The imaging detector 108 reads the response of the imaging signal 106 when directed on the markers 110 and targets 112, where the signal response information is provided to the controller 102. A radiation source 116 receives instructions from the controller 102, where the information includes on/off operation, beam intensities and modulation, for example. An uncollimated radiation beam 118 is directed onto a multi-leaf collimator (MLC) 120 and a linear accelerator (LINAC) jaw assembly 122, where a collimated radiation beam 124 is directed onto the target 112. Information from a treatment plan 124 is provided to the controller 102 that includes dosimetric information for the radiation therapy treatment. FIG. 1(b) shows a typical MLC 120 and target 112, where the MLC 120 has a sequence of leaf pairs 126 made from individual opposing leaves 128. Each leaf 128 can be independently controlled by a dedicated motor (not shown) that is commanded by the controller 102. Similarly, the LINAC jaws 122 may be controlled in this manner. Further shown in FIG. 1(b) are the many leaf ends 130 that, when in combination, defining a collimation aperture 132.

Figure 2:
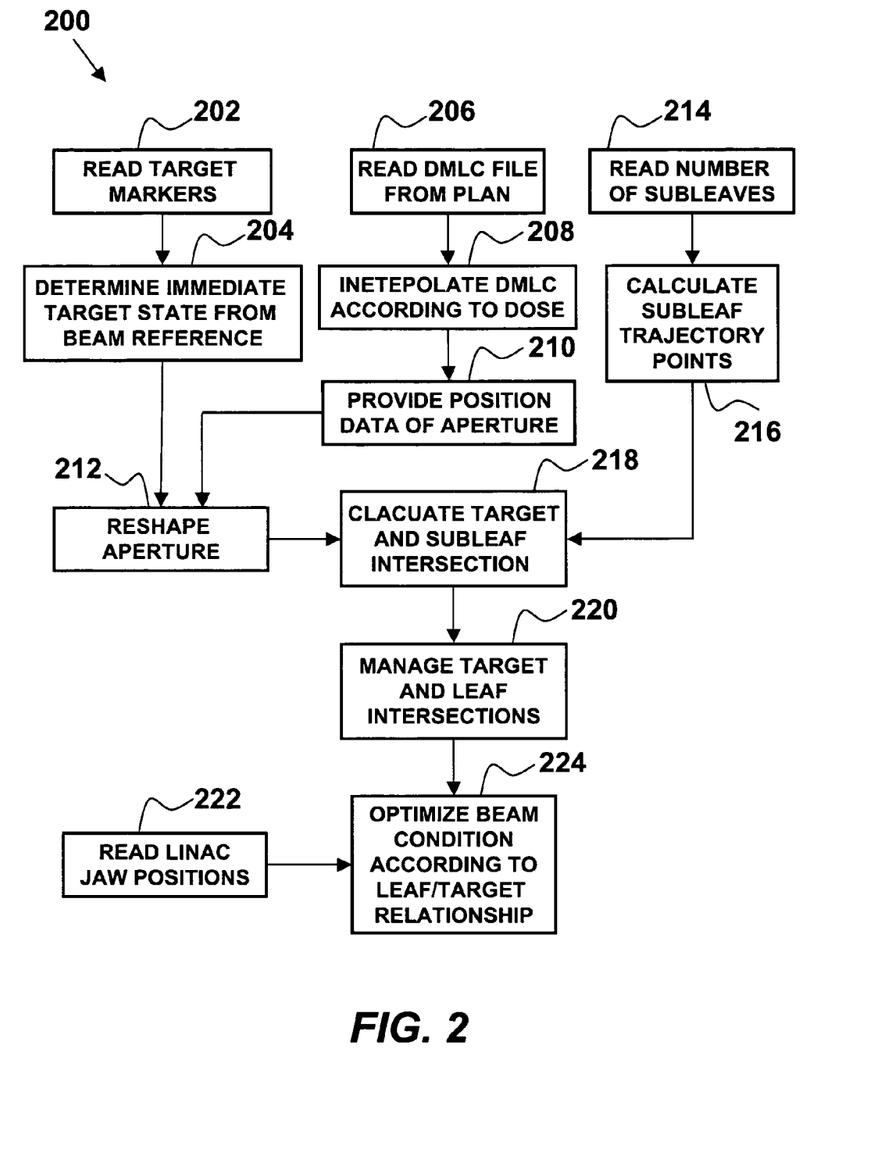
FIG. 2 shows a flow diagram of the method to track three-dimensional target motion with a dynamical multi-leaf collimator according to one embodiment of the present invention.

Shown in FIG. 2 is a flow diagram of the target tracking method 200 according to one embodiment of the present invention, where provided is continuous real-time monitoring and positioning of the DMLC 120 during on and off radiation exposure conditions of the radiation therapy treatment, where the method 200 accounts for target 112 and anatomical (not shown) motion relative to the collimated radiation beam 114. As shown, the method 200 includes reading the target markers 202, followed by determining immediate target state from the beam reference frame 204, where this step provides the instantaneous position, shape, size and orientation of the target 112 and tracks its three-dimensional motion with the MLC 120, according to the present invention. The determination of the immediate target state 204 includes using a prediction algorithm with the controller 102 to estimate a future position of the target 112, determine an initial position of the target 112 by monitoring external and internal target markers 110, use a rotation matrix to calculate rotational changes in the position of the target 112 relative to the radiation beam 118 formed by the angular orientation of the gantry and the MLC 120, use Cartesian coordinates along a DMLC plane to calculate an X-offset and a Y-offset of the target 112, where the offsets result from movement of the target 112 along a path of the radiation beam 118, and use Cartesian coordinates along an isocentric plane of the target 112 to calculate an X-translation and a Y-translation of the target 112. The isocentric plane is defined as the plane perpendicular to the principal axis of the radiation source.

Concurrent with reading the target markers 202, the method includes the step of reading leaf 128 positions from a DMLC file 206 of the treatment plan 106. Temporal interpolations of radiation doses are provided according to the treatment plan 106, where predetermined positions of the leaves 128 are provided that correlate to radiation dose segments along a total duration of a total irradiation of the target 112. The DMLC data are interpolated to determine the leaf 128 positions as a function of the prescribed dose 208. This information is used to provide initial position data 210 of the aperture(s) 132, where the leaf 128 positions are converted to common Cartesian coordinates with the origin at the isocenter and offset from the isocenter by a Δz value along the beam 114 path, where the (x, y) coordinates of the MLC leaf tips 130 are then determined.

Here, the DMLC leaf tip 130 information and the Cartesian coordinates and the isocentric plane of the target 112 information are provided to the controller 102, where the step of reshaping 212 the aperture 132 occurs. In such, the aperture reshaping step 212 includes displacing each (x, y) coordinate by the X-translation and Y-translation of the target 112 when the target state was determined 204, and joining the adjacent points according to the tip end 130 segments to form the shape of the reshaped aperture 132.

Figure 3:
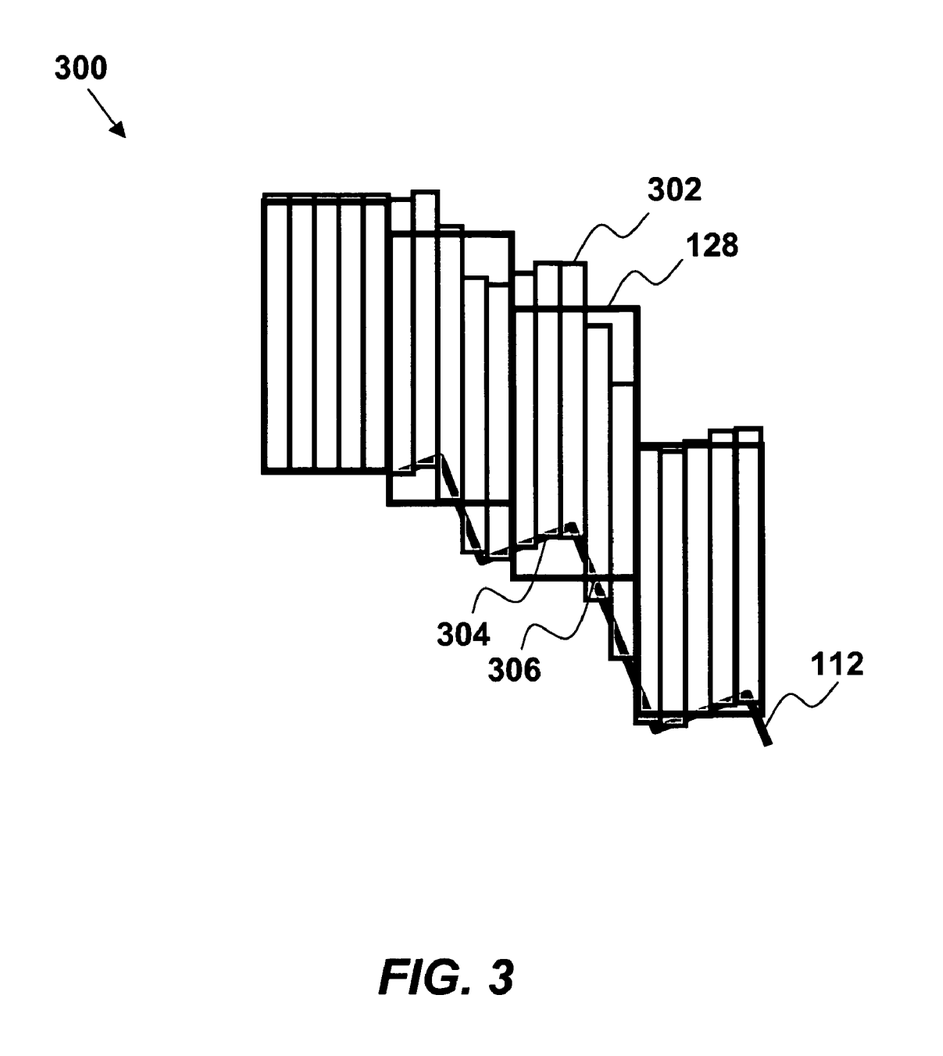
FIG. 3 shows a method to minimize the geometric and dosimetric error according to the present invention.

Referring now to FIG. 3, where shown is a diagram describing a method to minimize the geometric and dosimetric error 300 by positioning the leaves 128 so that the overdosed and the underdosed regions in the treatment plane are approximately equal, where the overdosed region is the area that is outside the calculated shape but open to the beam and the underdosed region is the area within the shape but under the leaves 128. This objective is achieved by dividing each leaf 128 into virtual "sub-leaves" 302. The intersections of each trajectory of the sub-leaf 132 with the segments of the shape are determined. The point of the parent leaf 128 intersection 306 of is then calculated as the average of the corresponding sub-leaf 134 trajectory intersections 304.

Referring again to FIG. 2, further in tandem with the marker reading step 202 and the MLC file reading step 206, is the step of reading a number of subleaves 214 (see FIG. 3) of each DMLC leaf 128, here the start and end points of each sub-trajectory are determined. From this, the step of calculating the subleaf trajectory points 216 is accomplished.

The controller 102 incorporates the reshaped aperture information 212 and the subleaf trajectory information 216 to perform the step of calculating the target and subleaf intersection 218 (shown as 304 in FIG. 3), where each point of the intersection 304 of each sub-trajectory with the segments of the modified shape are determined.

The method 200 is now in a state to manage the target and leaf aperture intersection information 220. The intersection management 220 includes determining if there is intersection between the target 122 and aperture 132, where if a condition no intersection exists, the method 200 queries if any other subleaves 302 intersect the target 112? In the event that no other subleaves 302 intersect, all the leaf pairs 126 are positioned at the center and are separated by the minimum closed leaf distance (~50 µm) and a beam hold condition is deemed to be false. Conversely, in the event that a condition of at least one other subleaf 302 does intersect the target 112, the method 200 uses only the intersecting subleaves 302 to calculate the average leaf 128 intersection, and a beam hold condition is deemed to be false. Further the intersection management step 220 queries for a single intersection, where a beam hold condition is deemed to be false. The intersection management step 220 also checks for multiple intersections, such as in a situation of a donut-shaped or a kidney bean-shaped target, or if the segment is coincident with the sub-leaf 302, resulting in infinite intersections. In the event any of these conditions are detected, the management step 220 records the multiple intersections 304 along the start and end points of the leaf 128 and the intersection points 304 are sorted in ascending order. The management step 220 then queries if the number of intersection points 304 is greater than two. If the parent leaf 128 intersecting points 306 exceeds two, a beam-hold condition is deemed true, and if the intersecting points 306 is less than two, the beam-hold condition is deemed false. Further, opposing leaves from a pair are positioned at the first and last intersections recorded by the management step 220.

According to the current invention, DMLC-based motion tracking is feasible for motion ranges equal to or greater than previous clinically observed motion ranges, for both conformal and IMRT delivery. For large target motion perpendicular to the leaf direction, beam holds may be implemented when the mechanical capabilities of the current DMLC motors are exceeded.

The method 200 uses the information from the management step 220 to the execute the step of optimizing the beam condition according to the leaf 128 and target 112 relationship 224, where the point of intersection 306 of each leaf 128 is calculated for each leaf 128 from the average of the corresponding sub-leaf 302 intersections. Concurrently, the method 200 reads the LINAC jaw positions 222, where this information is compiled with the leaf intersection 306 data and the leaf/target optimization step queries if the target moved beneath any jaw 122 resulting in an open leaf pair 126 being positioned under one or more jaws 122. If this condition does exist, a beam hold condition is deemed to be true, and if the condition does not exist, the beam hold condition is deemed to be false.

Figure 5:
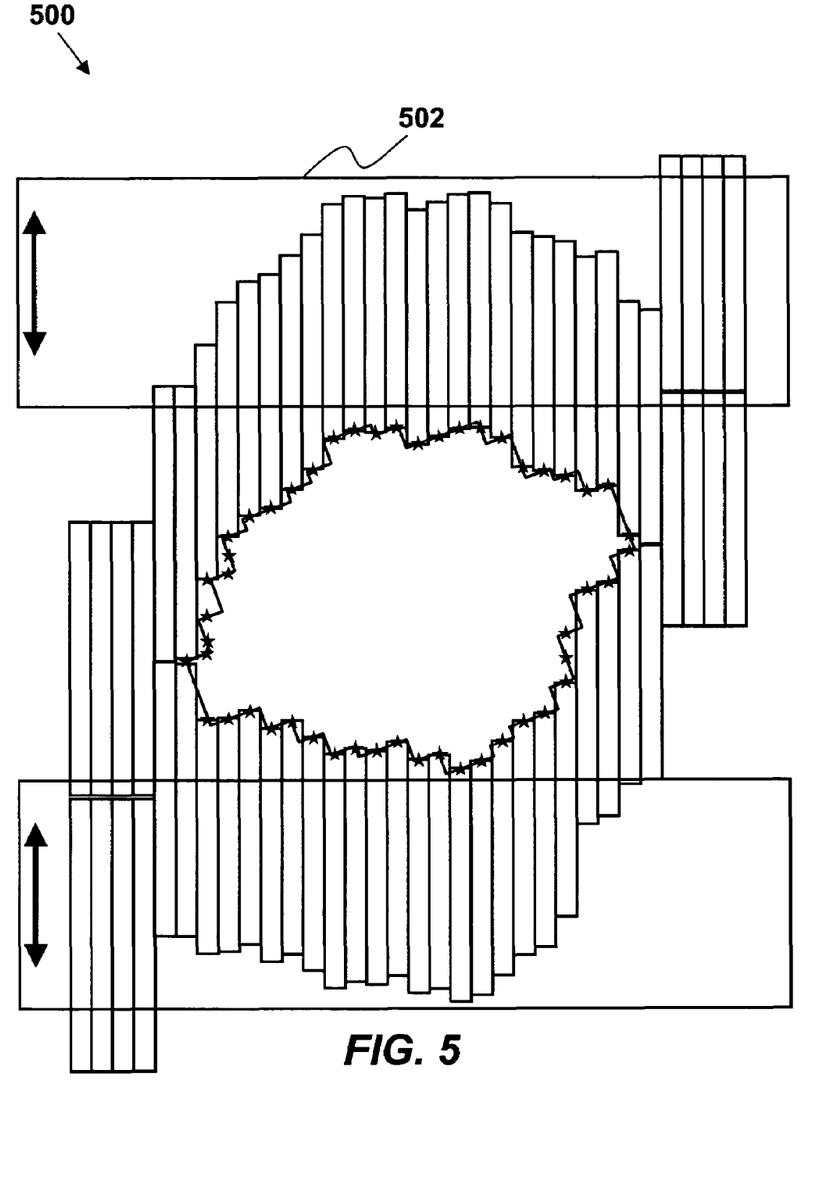
FIG. 5 shows minimization of leakage radiation by moving the MLC leaf pairs that do not participate in the tracking process under the nearest jaws according to the present invention.

There occurs a small but significant amount of radiation leakage through the tips of closed DMLC leaves. Minimization of such leakage radiation is accomplished by moving the DMLC leaf pairs that do not participate in the tracking process under the nearest jaws. In the process of tracking target motion perpendicular to the direction of leaf travel, leaves that are positioned at the periphery of an aperture at a given time instant may need to become part of the aperture in the next time instant. In order to ensure that a leaf pair does not have to move suddenly from beneath the jaws to form an aperture, some leaf pairs on either side of the original aperture are positioned at the center of the leaf opening for the leaf pairs defining the extent of the aperture and abut to its opposing leaf. The number of adjacent, closed leaf pairs is estimated from the extent of target motion in the perpendicular direction. Note that, if there are multiple open apertures on either side of an adjacent leaf pair, then these (closed) leaves are directed at the midpoint (along the direction parallel to leaf motion) of the leaf positions corresponding to the nearest open leaf pairs on each side.

In one aspect of the invention, sending and retrieving leaf pairs from under the jaws to the adjacent state is performed using a below the maximum velocity for this MLC to ensure this process does not contribute to a beam hold.

While most intrafraction motion can be considered to be somewhat predictable in terms of magnitude and/or frequency, a variety of situations may occur that require the dose delivery to be paused. For example, the position monitoring system may detect irregular motion due to large shifts in patient position during treatment, a sudden change in respiratory pattern, bowel movement, swallowing, coughing, etc. In some cases, the motion may be faster than the MLC leaves can track or, the motion may necessitate one or more MLC leaves to move beyond their travel range. Or, the desired aperture may move beneath the primary jaws. In all such situations, the algorithm determines the magnitude of the change from the position monitoring system and asserts a beam hold while the anomalous condition persists. At the same time, the DMLC leaves continue to track target motion so that dose delivery can be resumed as soon as the anomalous condition stops, thus maximizing delivery efficiency.

Figure 4:
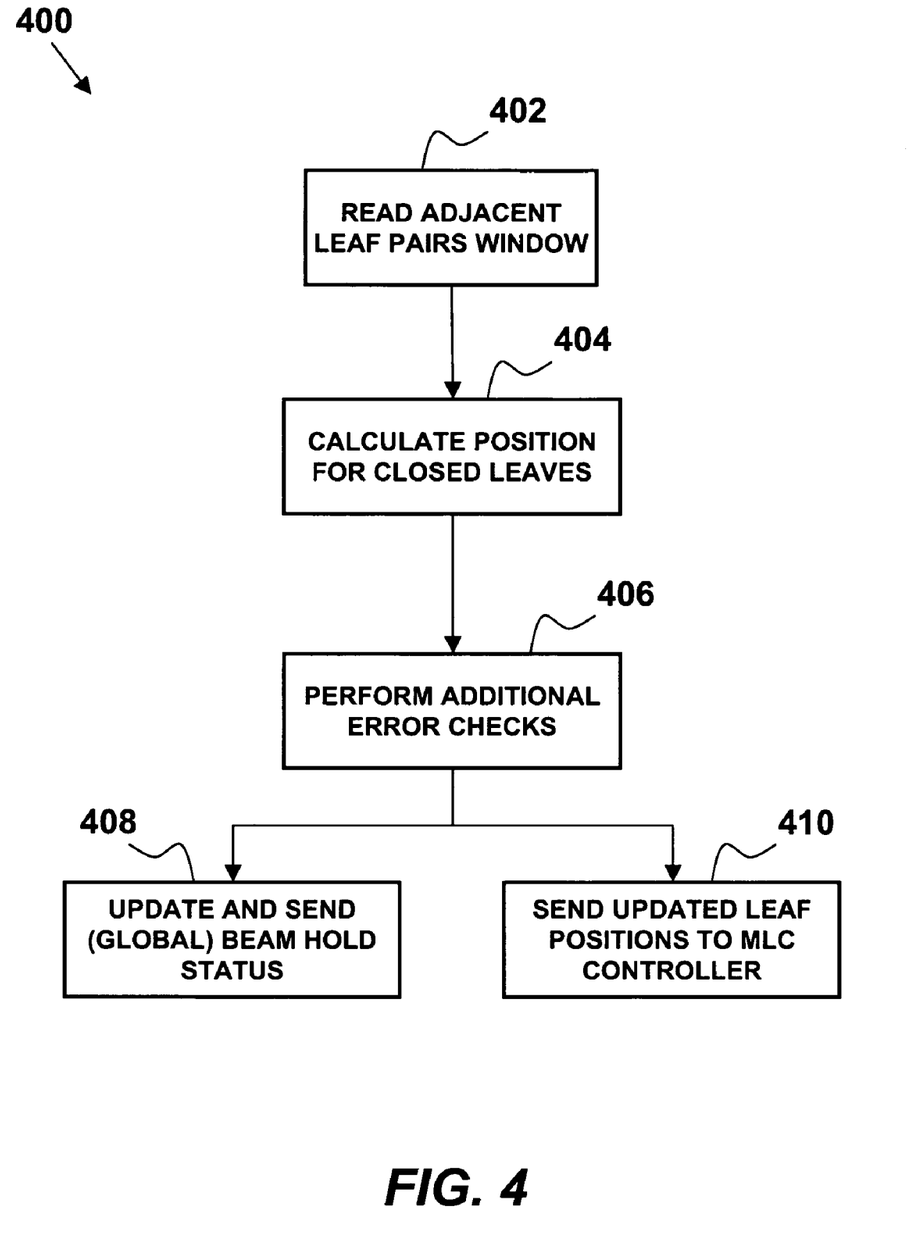
FIG. 4 shows a flow diagram of the method leaf pair management according to the present invention.

FIG. 4 shows the aspect of the leaf pair management method 400 that begins with reading adjacent leaf pairs 402 (shown as 126 in FIG. 1(b)), followed by the step of calculating leaf positions 404 for closed leaves 126. In the step of calculating leaf position 404, only those leaf pairs 128 that are not under the Y-jaws 502 (see FIG. 5) are considered, where if the leaf pair 128 is open, the position is understood to have already been calculated in the previous loop, and if the leaf pair 128 is not open, the method 400 queries if adjacent leaf pairs 128 on both sides are closed? If the condition exists that adjacent leaf pairs 128 on both sides are closed, then the bound leaf pair 128 is moved at maximum velocity towards ~2.5 mm under the nearest X-jaw 504 to limit radiation leakage. If the condition exists that the adjacent leaf pairs 128 on both sides are not closed, the method 400 determines the nearest open aperture(s) 132 on both sides of the leaf pairs 128. Simultaneous conditions are seen from this step: if there are open apertures on either side of closed leaf pair, the leaves are moved at maximum velocity towards the average of the nearest left and nearest right open leaf pairs 128; if there are open aperture(s) on only one side of the closed leaf pair 128, send the leaves at maximum velocity towards the midpoint of the nearest open leaf pair 128; and if there are no open apertures, the beam hold condition is deemed true and a warning message is sent.

From the resultant condition of the calculating of leaf positions 404, provided is the step of performing additional error checks 406. This method 400 queries if any leaf pair 128 overlap? If the condition is affirmative, a warning is issued and a beam hold condition is deemed true. If the condition is negative, the method 400 queries if the leaves are separated more than the maximum allowable distance? If this condition is affirmative, the leaves 128 are moved at maximum velocity towards each other, and a beam hold condition is deemed true.

From the step of performing additional error checks 406, simultaneous information is sent to update and send (global) beam hold status 408, and send updated leaf positions to the controller 102.

In one embodiment of the invention, a DMLC-based dynamic motion compensation system is provided that includes a 3D optical position monitoring (Varian RPM v1.7) integrated with a-real-time DMLC controller. As illustrated in FIGS. 6-9, target motion in the beam's view may be classified into the following types:

1. Rigid translation along the beam direction, resulting in magnification/demagnification in the treatment plane.

2. Rigid, in-plane rotation.

3. Rigid translation in the treatment plane (i.e., the isocentric plane perpendicular to the beam 80 axis) including motion both parallel and perpendicular to MLC leaf travel direction.

4. Rigid, out of plane rotation and deformation (both of which result in a change in the target shape in the beam's view).

Figure 6:
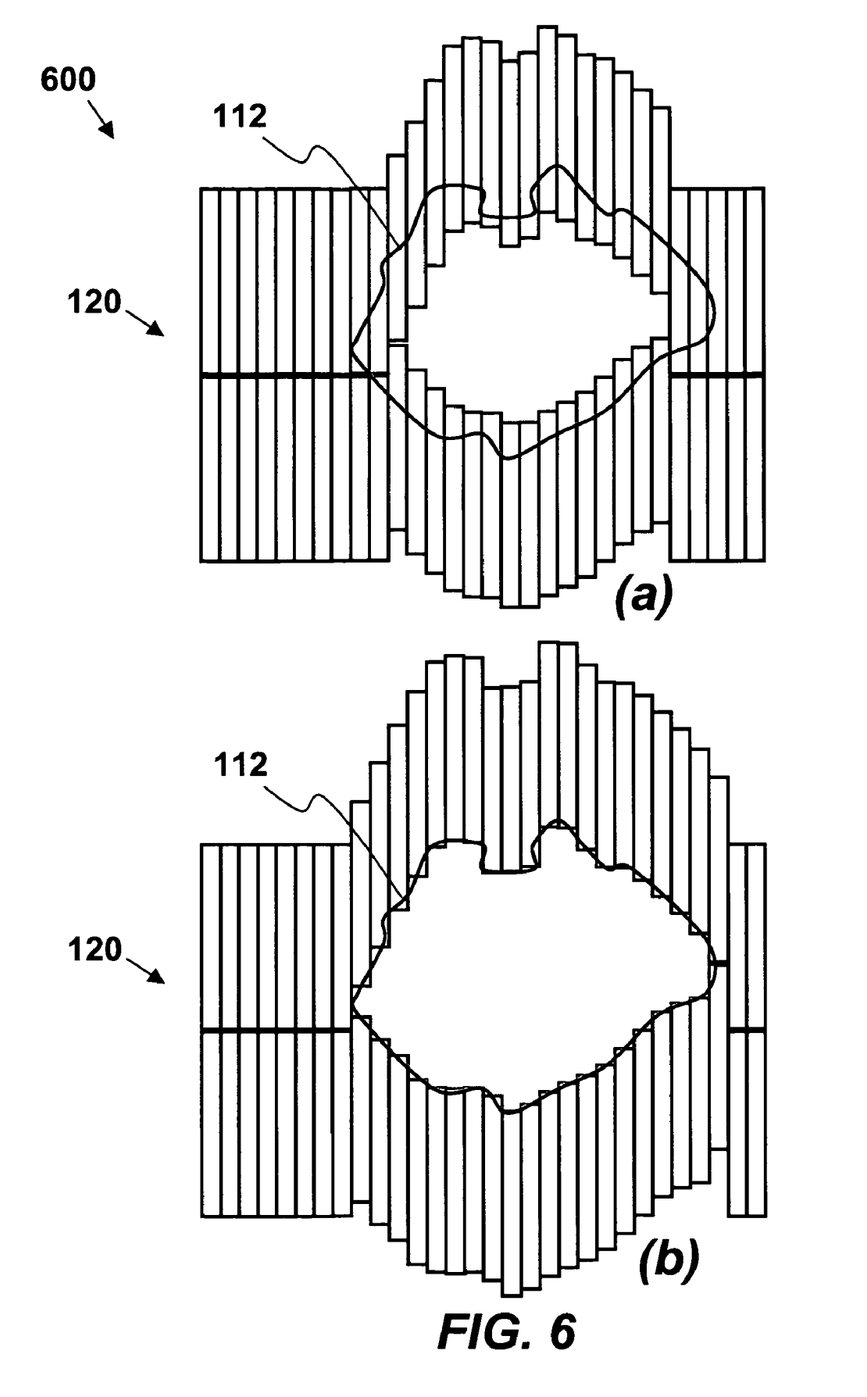
FIGS. 6-9 show tracking of target motion in the beam's view according to the present invention.
Figure 7:
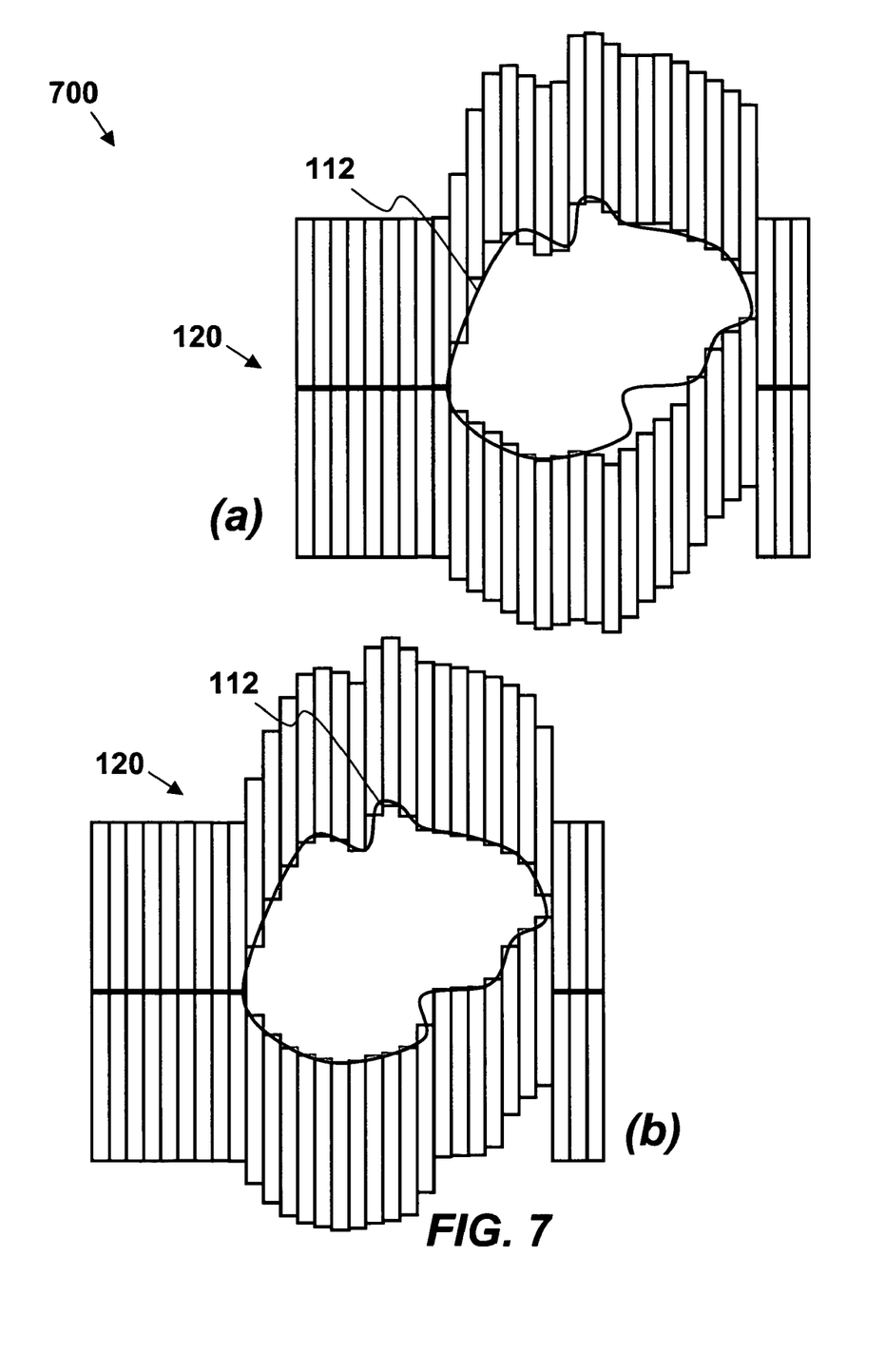
Figure 8:
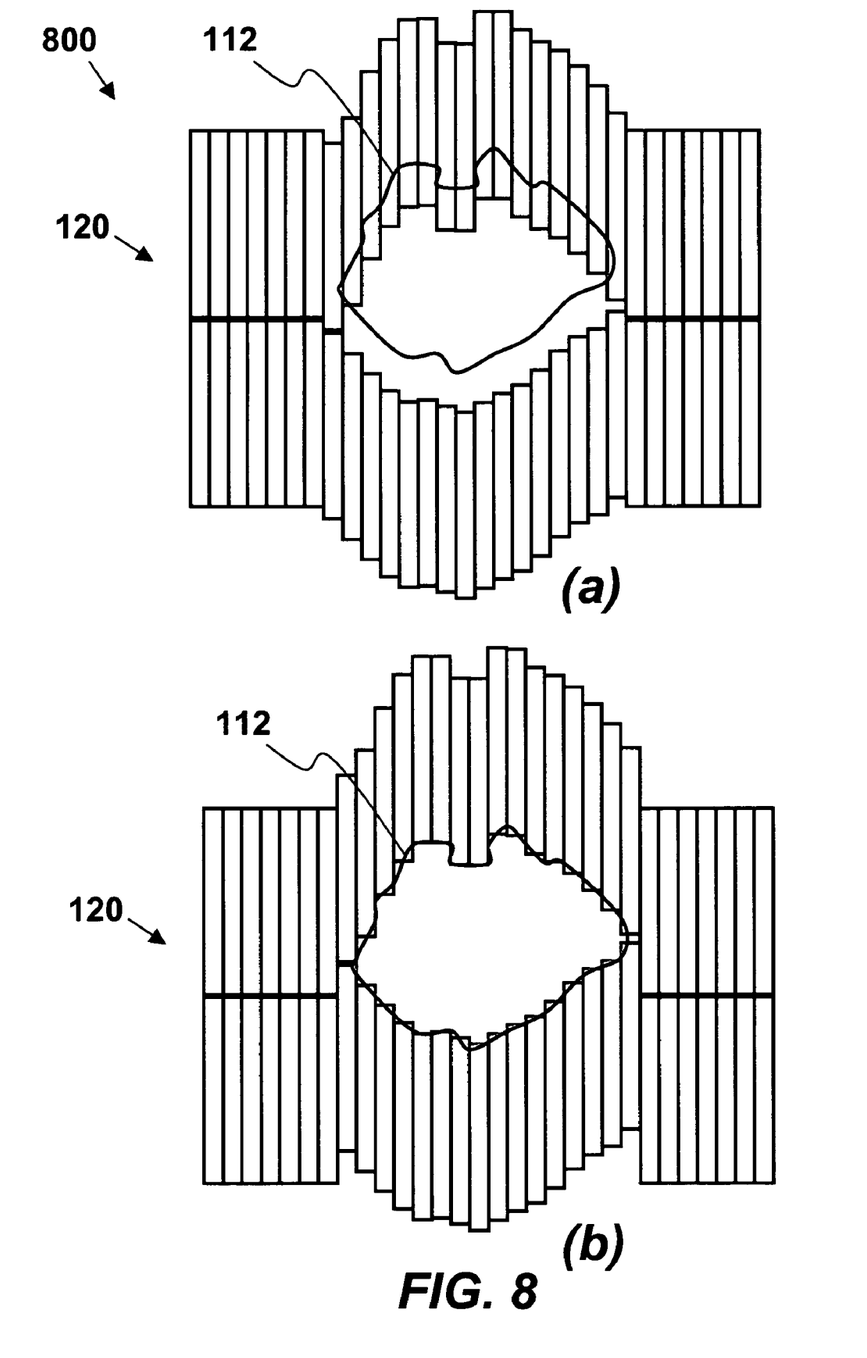
Figure 9:
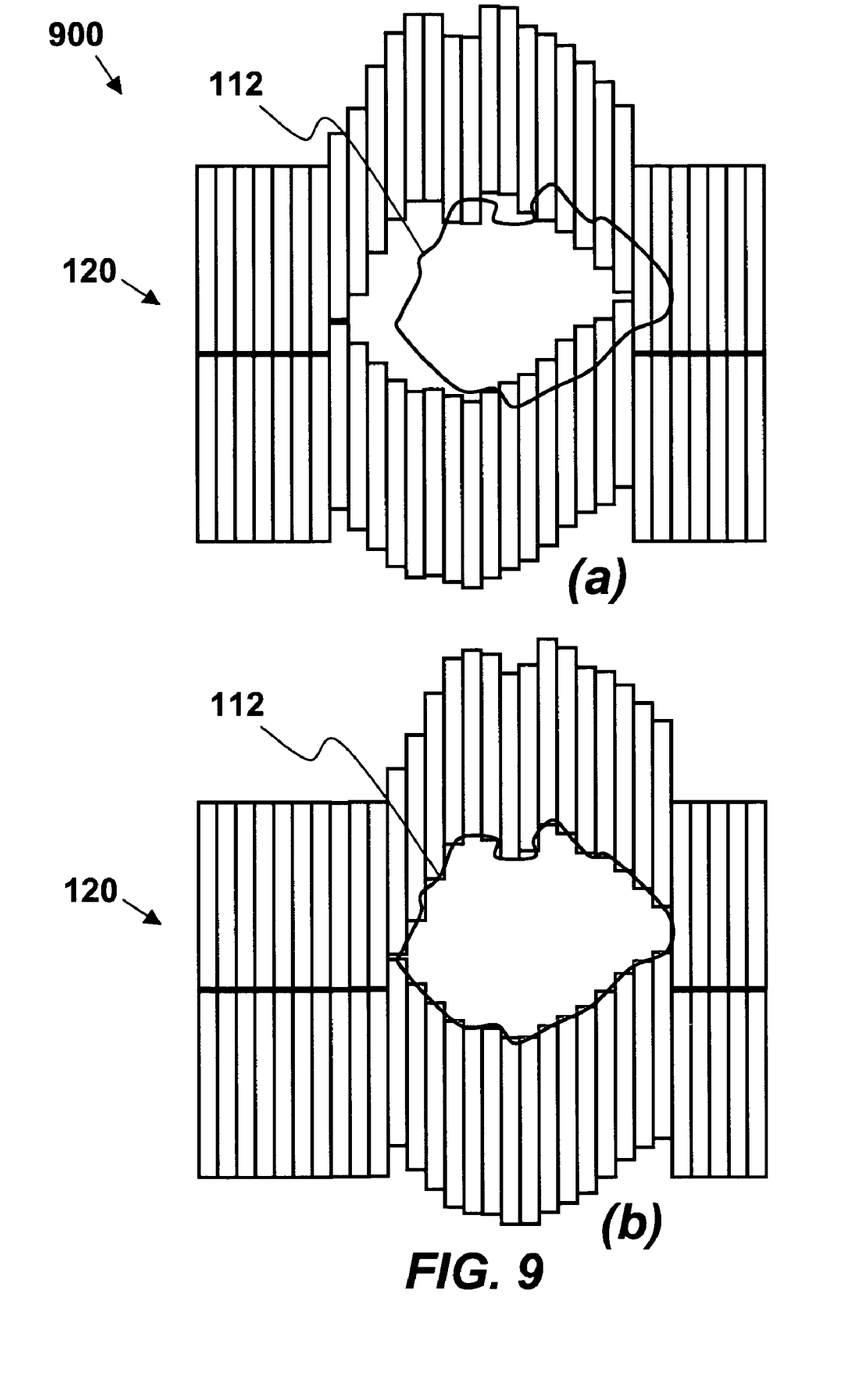

FIGS. 6(*a*) and 6(*b*) show motion along the beam axis 600 is accounted for by scaling the beam aperture by the ratio of the isocenter distance to the beam-target distance, and FIGS. 7(*a*) and 7(*b*) show in-plane and out of plane rotation and deformation 700 are tracked by interpolating leaf indices and positions according to the current embodiment. FIGS. 8(*a*) and 8(*b*) show tracking of target motion detected along the leaf direction 800 is performed through leaf translation FIGS. 9(*a*) and 9(*b*) show motion perpendicular 900 to the leaf direction is tracked by interpolating leaf indices and positions according to the current embodiment. Both conformal and IMRT beams may be delivered, for example.

The current invention further provides a method to dynamically recalculate new beam apertures so as to account for the geometric changes in the volume of interest as observed in the beam's eye view, a mathematical relationship between the 4D motion plan and relocation vectors is provided. The 4D plan accounts for maximum leaf velocity and the velocity, position and shape of the target(s) as well as organs at risk (OARs). During delivery, the planning 4D images use a starting point to identify target(s) and OARs in the anatomical volume. Subsequently, using information from the volumetric position monitoring algorithm 200 and 400, accounts for the instantaneous position and shape of both target(s) and OARs. In this phase, motion is used as a degree of freedom, rather than a constraint. As a target moves in and out of the beam line with respect to an OAR (e.g., a lung tumor overlapping and moving away from the spinal cord), this information is used to reduce or escalate the dose. In one embodiment, the tracking algorithm implements such modulation through judiciously asserting beam holds. This strategy can only be implemented reliably when real-time volumetric information is available, as provided by the aspects of the current invention, advancing realization of true 4D adaptive radiotherapy delivery.

Figure 10:
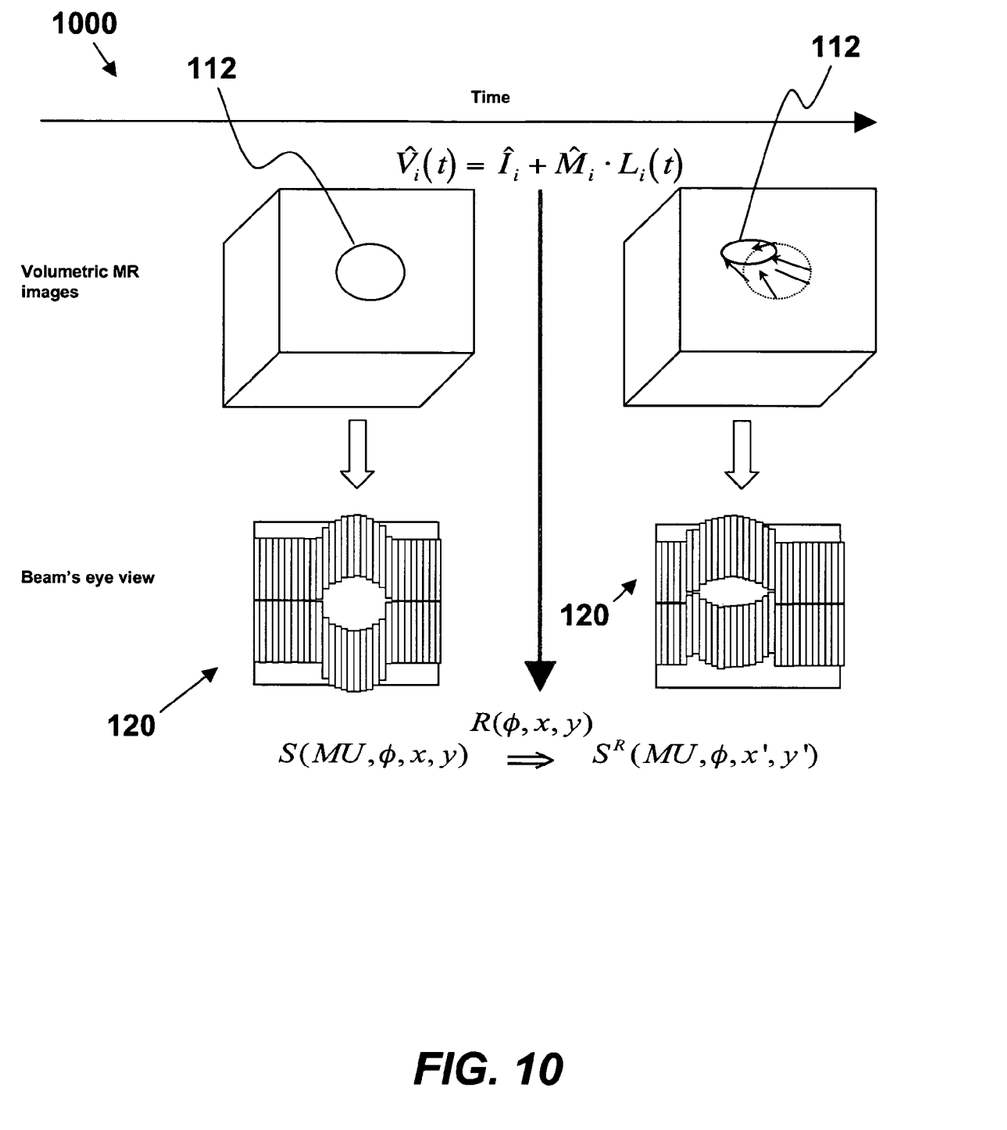
FIG. 10 shows a relationship diagram between the volumetric data and the corresponding real-time tracking of the MLC when the relocation vector is applied.

All forms of target motion are accounted for by remapping the displacement of each point of the original shape L(MU, x,y) to a new location (x', y') on the treatment plane. This process can be represented as Relocation vectors that are defined as a function of respiratory phase φ as well as the number of monitor units (MU) using information from a 4D deliverable plan. Relocation vectors are re-written as:

$$S(MU, \phi, x, y) \xRightarrow{R(\phi,x,y)} S^R(MU, \phi, x', y'),$$

where R(x,y) is termed as the relocation vector. For rigid body motion, R(x,y) is constant for the entire shape. The nature of the process that causes the 3D displacement (translation, rotation or deformation of the target) is transparent to this calculation. FIG. 10 shows relationship diagram 1000 between the volumetric data received from the image detector 108 and the corresponding real-time tracking of the MLC 120 of the target 112 when the relocation vector is applied.

According to the current invention, the tracking MLC will have a good "first-guess" of what the anatomy looks like at a particular respiratory phase. Any deviation from the phase-dependent geometry occurring during treatment is compensated for by modifying the beam aperture according to the relocation vectors. This approach can result in fewer beam holds, due to the fact that the magnitude of deviations for two instances of the same respiratory phase will typically be smaller than that of deviations from an "average" phase.

There exists an inherent temporal latency associated with the processes of detecting target motion, calculating new positions by the tracking algorithm and the response time of the MLC leaves. In order to compensate for such latency, the position of the target at time T(t+Δ) is predicted, where Δ represents the amount of temporal latency (measured to be ~160 ms for our lab system$_{40}$). In the present invention, the method can uses prediction algorithms such as neural networks, autoregressive moving average models, Kalman filters, adaptive filters, modified linear adaptive filter, adaptive and Kalman filters.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example, the principal component of target motion perpendicular to MLC leaf motion may be accounted for by moving the carriages that hold each MLC leaf bank and the residual motion can be accounted for by moving multiple MLC leaves. Furthermore, while the present embodiment has been described for conformal and step-and-shoot and dynamic intensity modulated radiation deliveries, extension of this algorithm to other delivery techniques such as conformal and intensity-modulated arc therapy will be relatively straightforward. While the current embodiment describes a purely geometric reshaping of the MLC apertures these teachings can be combined with previously developed dosimetric optimization techniques in order to deliver real-time dosimetrically optimized treatments that account for target and anatomical motion. Although the current invention is described to address intrafraction motion management, the teachings can be applied with minimal modifications toward the management of other forms (e.g., interfraction) of patient motion.

All such variations are considered to be within the scope and spirit of the present invention as defined by the following claims and their legal equivalents.

What is claimed:

1. A method of continuous real-time monitoring of anatomy and continuous real-time beam positioning using multi-leaf collimators (MLC) during on and off radiation exposure conditions of radiation therapy treatment in order to account for target and anatomical motion relative to a radiation beam comprising:
   a. using a prediction algorithm within a controller to estimate a future position of a target in relation to a radiation source reference frame;
   b. determining a position, a size, a shape and an orientation of said target according to a frame of reference of said radiation source;
   c. providing said determined target information to a controller;
   d. determine an initial position of each leaf of said MLC;
   e. provide a treatment plan to said controller from a treatment plan data file;
   f. provide temporal interpolations of radiation doses and a respiratory phase according to said treatment plan, whereby predetermined positions of said leaves are provided that correlate to radiation dose segments along a total duration of a total irradiation of said target;
   g. using Cartesian coordinates having an origin at an isocenter of an isocentric plane of said target to establish an initial position of aperture ends of said leaves;
   h. providing said initial position information of said aperture ends to said controller;
   i. determining an aperture end width and determining a midpoint of said aperture end for each said leaf;
   j. providing said width and midpoint information to said controller, wherein said controller directs motors to position said MLC midpoint aperture ends according to said initial position information and said provided target information;
   k. positioning each said aperture end midpoint to intersect a single point of a convolution of said target and said isocenter of said isocentric plane; and
   l. providing radiation source hold conditions, wherein said hold condition is according to predetermined undesirable operational and/or treatment states.

2. The method of claim 1, further comprising calculating optimal radiation source jaw positions, wherein said jaw position optimization comprises;
   a. using Cartesian coordinates in a plane that is transverse to said radiation source having an origin concentric to said source to determining initial positions of said jaw;
   b. providing said jaw positions to said controller;
   c. dynamically positioning exposure ends of said jaws, wherein said jaw ends are positioned proximal to said aperture ends of said MLC.

3. The method of claim 2, wherein said proximal position is from 0 to 20 said leaf widths along a first axis of said jaw coordinate system and is from 0 to a maximum travel range of said leaf along a second axis of said jaw coordinate system.

4. The method of claim 1, wherein said prediction algorithm is selected from a group comprising neural networks, autoregressive moving average models, Kalman filters, adaptive filters, modified linear adaptive filter, adaptive and Kalman filters.

5. The method of claim 1, wherein said target position, size and shape determination comprises:
   a. determine an initial position of a target by monitoring at least one external target marker and/or at least one internal marker;
   b. using a position prediction algorithm to estimate a future position of said target;
   c. using a rotation matrix to calculate rotational changes in said position of said target relative to said radiation apertures;
   d. using Cartesian coordinates along an MLC plane to calculate an X-offset and a Y-offset of said target, wherein said offsets result from movement of said target along a path of said radiation source; and
   e. using Cartesian coordinates along an isocentric plane of said target to calculate an X-translation and a Y-translation of said target.

6. The method of claim 1, wherein said predetermined undesirable operational and/or treatment state is selected from a group comprising when said target moves below one or more said jaws, when said leaf aperture end intersects more than a single point of said convolution of said target and said isocenter of said isocentric plane, when no said apertures exist in said MLC plane, when any said leaves in a leaf pair overlap, and when said leaves are separated more that a maximum allowable distance.

7. The method of claim 1 further comprises dynamically moving MLC carriages in a direction perpendicular to leaf motion in order to track a principal component of motion along said direction perpendicular to said MLC leaf motion, whereby moving a plurality of MLC leaves in a manner to account for components of said target and anatomical motion along a direction of leaf travel.

8. The method of claim 1, wherein said radiation beam is a particle beam, whereas said continuous real-time beam positioning is performed using a particle actuator, whereby said particle actuator shapes said particle beam according to said convolution of said target and said isocenter of said isocentric plane.

* * * * *